(12) United States Patent
Figueroa Saavedra et al.

(10) Patent No.: US 9,583,302 B2
(45) Date of Patent: Feb. 28, 2017

(54) CONVERGENT PHOTON AND ELECTRON BEAM GENERATOR DEVICE

(75) Inventors: Rodolfo Figueroa Saavedra, Temuco (CL); Mauro Valente, Cordoba (AR)

(73) Assignees: UNIVERSIDAD DE LA FRONTERA (CL); UNIVERSIDAD NACIONAL DE CORDOBA (AR)

( * ) Notice: Subject to any disclaimer, the term of this patent is extended or adjusted under 35 U.S.C. 154(b) by 446 days.

(21) Appl. No.: 14/112,429

(22) PCT Filed: Apr. 19, 2012

(86) PCT No.: PCT/IB2012/051983
§ 371 (c)(1),
(2), (4) Date: Jan. 6, 2014

(87) PCT Pub. No.: WO2012/143893
PCT Pub. Date: Oct. 26, 2012

(65) Prior Publication Data
US 2014/0112451 A1 Apr. 24, 2014

(30) Foreign Application Priority Data

Apr. 20, 2011 (CL) .................................. 898-2011

(51) Int. Cl.
*H01J 35/14* (2006.01)
*H05G 1/58* (2006.01)
(Continued)

(52) U.S. Cl.
CPC ............ *H01J 35/14* (2013.01); *A61N 5/1042* (2013.01); *A61N 5/1084* (2013.01); *G21K 1/025* (2013.01);
(Continued)

(58) Field of Classification Search
USPC .................................. 378/143, 147, 149, 65
See application file for complete search history.

(56) References Cited

U.S. PATENT DOCUMENTS

| 3,969,629 A | 7/1976 | McIntyre |
| 5,222,114 A * | 6/1993 | Kamata ................ G01N 23/046 378/125 |
| 2010/0133446 A1 | 6/2010 | Balakin |

FOREIGN PATENT DOCUMENTS

| WO | WO 02/058557 | 8/2002 |
| WO | WO 2004/006270 | 1/2004 |
| WO | WO 2008/118198 | 10/2008 |

OTHER PUBLICATIONS

International Search Report for International Application No. PCT/IB2012/051983 mailed Oct. 29, 2012, 16 pages.

* cited by examiner

*Primary Examiner* — Kiet T Nguyen
(74) *Attorney, Agent, or Firm* — Merchant & Gould P.C.

(57) ABSTRACT

A piece of scientific/technological equipment is presented for the generation of a convergent photon beam for radiotherapy or other applications. This equipment consists of adequately modifying the trajectory of an electron beam from a linear accelerator (LINAC) by applying magnetic and/or electric fields. These electrons perpendicularly impact the surface of a curved material that has a particular curvature ratio (anode), thus generating X-rays. The interaction of the electrons with the atoms of the anode's material generate X-rays with a non-isotropic angular-spatial distribution, with a greater concentration in the focal direction, which is defined by the geometry of the anode. A curved collimator with an adequate curvature ratio is attached to the back of the anode. The collimator is made up of an array of a great number of small holes that point toward the focal point. This device transmits X-rays solely in the focal direction. The Summary Figure presents a typical configuration of the invention that has been presented.

6 Claims, 13 Drawing Sheets

(51) Int. Cl.
*A61N 5/10* (2006.01)
*G21K 1/02* (2006.01)
*G21K 1/08* (2006.01)
*H05G 1/02* (2006.01)

(52) U.S. Cl.
CPC .............. *G21K 1/08* (2013.01); *H05G 1/02* (2013.01); *H05G 1/58* (2013.01); *A61N 2005/1089* (2013.01); *A61N 2005/1091* (2013.01); *A61N 2005/1095* (2013.01); *H01J 2235/087* (2013.01)

CONVERGENT PHOTON AND ELECTRON BEAM GENERATOR DEVICE

CROSS-REFERENCE TO RELATED APPLICATIONS

This application is a National Stage Application of PCT/IB2012/051983, filed 19 Apr. 2012, which claims benefit of Serial No. 898-2011, filed 20 Apr. 2011 in Chile and which applications are incorporated herein by reference. To the extent appropriate, a claim of priority is made to each of the above disclosed applications.

BACKGROUND

From the discovery of the X-ray in 1895 until now, the emission of a radiation ray, at any energy range, is essentially divergent and the intensity is a function of the distance between it and the emission source (inverse square law). This is due to the X-ray production mechanism; in other words, electrons that impact a target. There are currently several ways to generate X-ray beams, each with a determined source size and a specific, always-positive divergence. The X-ray beams employed in radiotherapy are divergent.

The expected objective of radiotherapy is, by using X-rays, to achieve a high X-ray flow zone within a specific volume. These X-rays would then deposit their energy. The energy deposited per unit mass is known as dose in radiotherapy. Since the beam that is used is noticeably divergent, several beams (fields) aimed at the volume of interest must be employed. As is widely known, the depth dose for an X-ray beam is dependent on an exponential downward curve according to the depth, with a maximum value near the surface. A multi-field application allows for a maximum dose in the interest volume (tumor site), despite the fact that the dose values in the surrounding areas are lower than those at the tumor site. These dose values are significant as they have higher values than what is tolerable in some cases, which can prevent the use of an effective dose in the tumor.

More refined techniques such as Intensity Modulated Radio Therapy (IMRT) or arc therapy improve and conform the maximum flow volume of X-rays, thus lowering dose levels in neighboring tissues and organs, though this decrease is not significant. A dose value decrease of up to 80% in tissues and organs near the interest zone has currently been achieved in relation to the dose in the interest zone. Treatment planning, however, continues to be complex. A decrease of collateral effects caused by radiation is always attempted, though their complete elimination is impossible.

Figure 1:
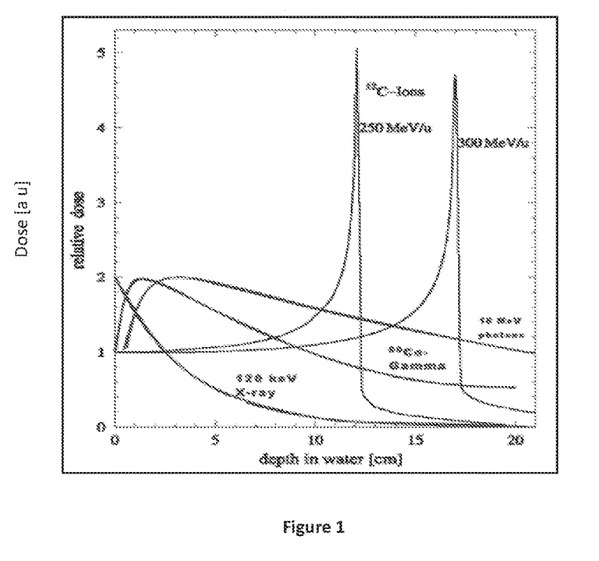
FIG. 1 shows a relative depth dose for the different techniques used in radiotherapy.

A radiotherapy technique that has lower collateral effects and greater radiobiological effectiveness at the tumor site is that of hadrontherapy. This technique uses hadrons (protons or heavier nuclei) to deposit high doses at the tumor site that are very conformed, that is to say, limited to that area. The cost of this technique, however, is much higher than conventional photon or electron methods, precluding its use for many patients. It is also rarely available at hospitals and health and treatment centers. FIG. 1 shows a sketch comparing the relative depth dose of the most widely used radiotherapy techniques.

This invention proposes the use of a device able to generate a convergent photon beam with advantages that are significantly greater than the conventional external radiotherapy technique and the hadrontherapy techniques, the latter catalogued as being those that provide better results.

Figure 2A:
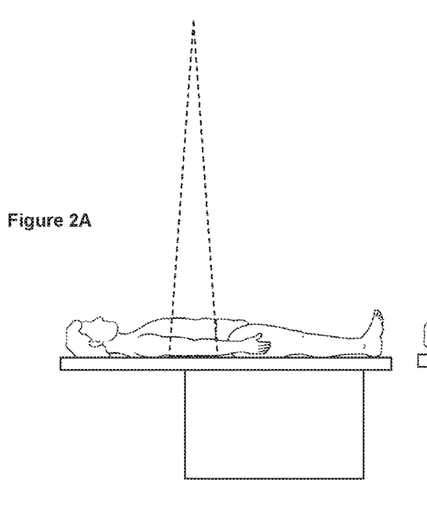
FIG. 2a shows a diagram of the traditional X-ray radiotherapy.
Figure 2B:
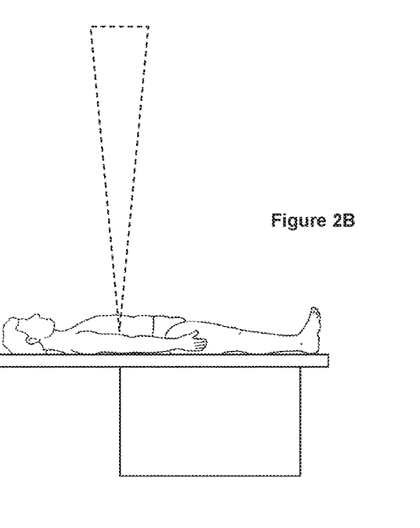
FIG. 2b shows a diagram of a convergent X-ray radiotherapy.

From a comparative point of view, conventional conformal radiotherapy techniques or IMRT (the latter being better): administer a greater superficial dose; are a greater risk to healthy organs; require fractioning and a more complex planning system; require more energy and, therefore, more costly bunkers; not all tumors are accessible; thus rendering the techniques less effective. The advantages of these techniques are that a greater volume is treated and the positioning system is simpler. FIG. 2 shows the fundamental difference between the conventional method, (a), and the convergent method (b).

The convergent method, however, presents: lower surface dose, low dose in healthy organs; high dose in the tumor which does not require fractioning; simpler planning system; shorter treatment (one or two sessions); greater effectiveness and accessibility to most tumors; simpler refrigeration system; high energy is not required thus bunker shielding requirements are lower. The disadvantage is that, as the treated volume is smaller, a tumor scan and a more precise positioning system are required.

The only external photon method that is comparable, quality-wise, to the convergent technique of the invention being proposed is the arc therapy technique, also known as Tomotherapy, using photons with a linear accelerator (LINAC) that generates electron beams to produce the required X-rays. Arc therapy emulates convergence by using an angular scan around the isocenter (tumor site). Despite longer sessions and equally complex planning, however, each beam is still essentially divergent and the doses in healthy organs are not insignificant. Like the other conventional LINAC techniques, several sessions are required. Similar results can be obtained using a robotic device called a "Cyberknife".

The hadrontherapy technique presents the following: a low surface dose and is highly effective as it deposits a high dose depth in a very small site (Bragg peak, see FIG. 1). Hadrons and ions have high radiobiological effectiveness (protons are 5 times more effective than photons) and complex positioning systems. However, a very complex installation is required, which includes a synchrotron able to accelerate particles to energies ranging from several hundred MeV to several GeV, high vacuum, and electrical and magnetic guide systems. Furthermore, the cost of a hadrontherapy system exceeds $100M USD. There are 28 hadrontherapy installations in the world's most developed nations and the technique continues to grow despite its high cost. Hadrontherapy is out of the question for Chile at present though Spain is evaluating the possibility of acquiring one of these installations in the next few years. Hadrontherapy has shown excellent results in patients with complex cancers as it is able to treat tumors that cannot be treated with photons. The cost of this therapy, however, means it is available to only a select few.

The convergent method employed by the invention presented here delivers low surface dose and is highly effective, as it deposits a high depth dose in a very small area ("peak focus"). Photons have less radiobiological effectiveness, but the dose deposited at the focus peak site can be up to 100 times greater than the dose on the surface, despite the attenuation effect. This compensates for the photons' lower radiobiological effectiveness and generates an even lower relative dose on the surface and in the healthy organs than that which is obtained in hadrontherapy. The positioning system, however, must be more precise than that of conventional techniques. All of the above will allow for the treatment of complex cancer cases as with hadrontherapy but with a less complex installation.

Furthermore, the cost of a LINAC plus a bunker and control building is in the $2 to 3 MUSD ranges, while a LINAC-adaptable convergence system may cost $0.5M USD or less, a noteworthy advantage in relation to the cost of a hadrontherapy installation which is almost two orders of magnitude greater. In this regard, a convergent system would function similarly to a hadrontherapy system but at a significantly lower cost.

Figure 3:
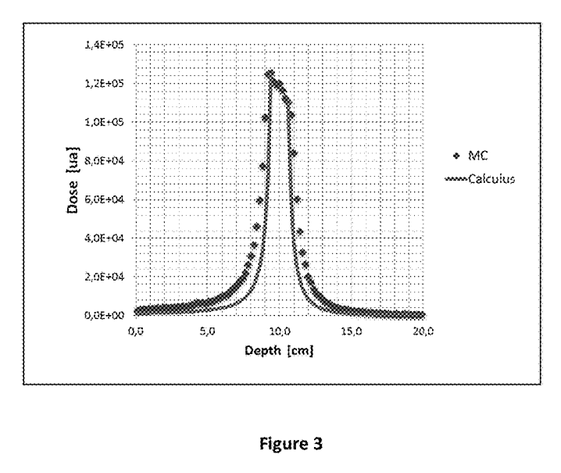
FIG. 3 shows a depth dose for a convergent photon beam at 0.4 MeV in a water phantom, compared to the theoretical results and MCS.

The first step taken prior to the development of this invention was the study of the effects of a photon beam's convergence on a specific material that was carried out by Monte Carlo Simulations (MCS) and theoretical calculations. FIG. 3 shows the curves of a depth dose corresponding to MCS and the theoretical results.

Devices currently exist that achieve beam convergence with a divergent X-ray beam based on the total reflection principle. The divergent X-rays enter a cone-shaped capillary, and the beams travel the length of it by total reflection inside the capillary until they reach the end. The exit section is smaller than the entry section, thus allowing a greater intensity to be achieved. In order to attain a significant increase in intensity, a set of these cone-shaped capillaries set in parallels is used. This makes up what is known as a poli-capillary and allows the entry area to be increased. However, as these devices employ the total reflection principle, its use is only advantageous with X-rays with energies below 50 keV, which limits its application in radiotherapy equipment, where the X-ray energy is much greater than the aforementioned amount. There is currently a great variety of X-ray focusing devices that use not only the total reflection principle but diffraction and/or refraction as well, though all of them can be used for low energy X-rays (<50 keV). For example, in astronomy, an X-ray telescope (Chandra and equivalents) obtains X-ray images of the Universe, allowing us to see emission sources, including black holes. This is a large-scale device (several meters) that is based on the same total reflection principle and uses reflector plates and other materials.

SUMMARY OF THE INVENTION

After considering existing devices, which are limited to low energy, and the results obtained from studies that were performed, this innovative idea of an electron- and convergent X-ray-generating piece of equipment was developed, appropriate for low, medium and high energies (<0.1 MeV, 0.1-1.0 MeV and 1>MeV respectively). This would also be the only way to achieve X-ray beam convergence at energies within the application's range in radiotherapy techniques.

Figure 4:
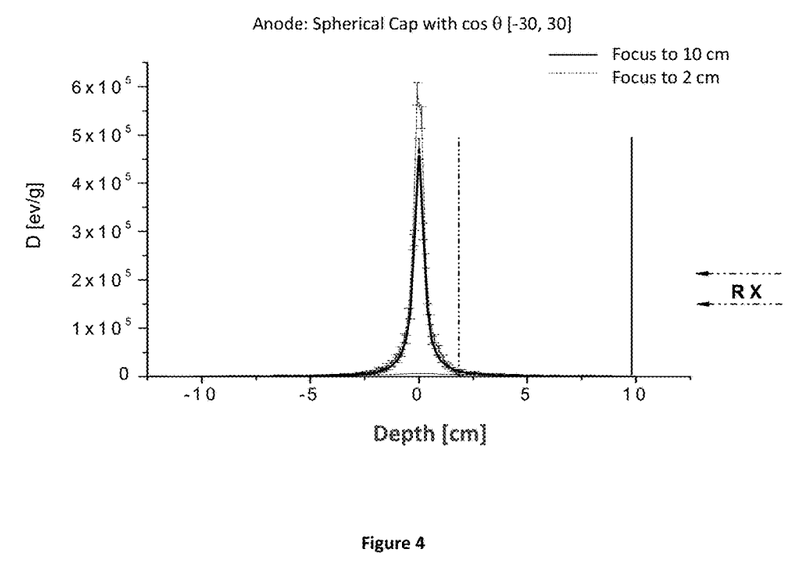
FIG. 4 shows a comparison of two dose profiles for convergent photons from two MCS for focal points at 2 and 10 cm from the surface of the phantom.
Figure 5:
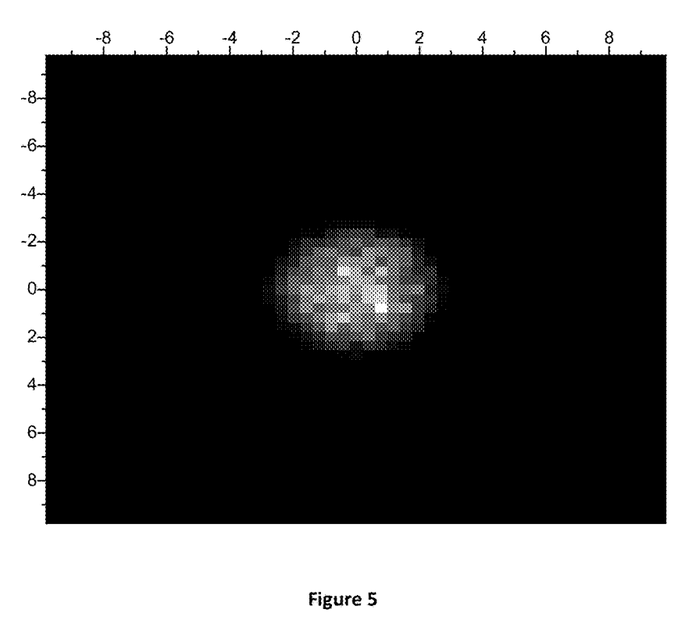
FIG. 5 shows a sectional view of a depth dose achieved by MCS for convergent photons, for a non-refined case.
Figure 6:
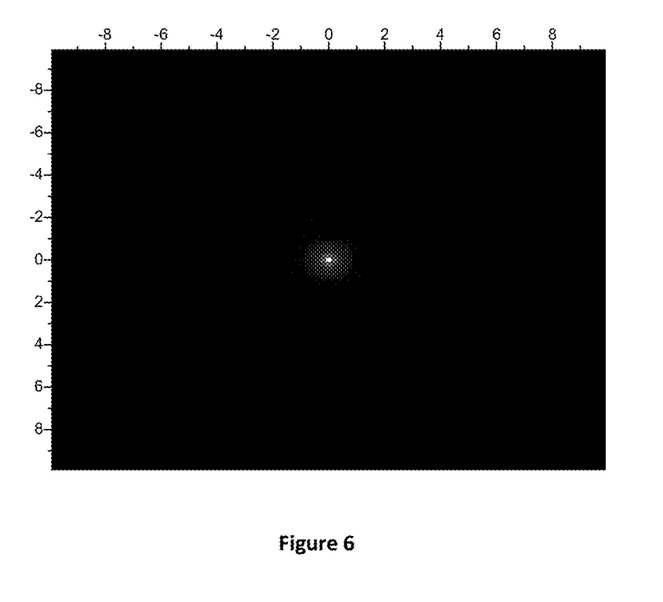
FIG. 6 shows a sectional view of a depth dose achieved by MCS for convergent photons, generated by the electrons that impact on an anode cap and then pass through a perforated cap-style poli-collimator similar to those proposed in this invention.
Figure 7:
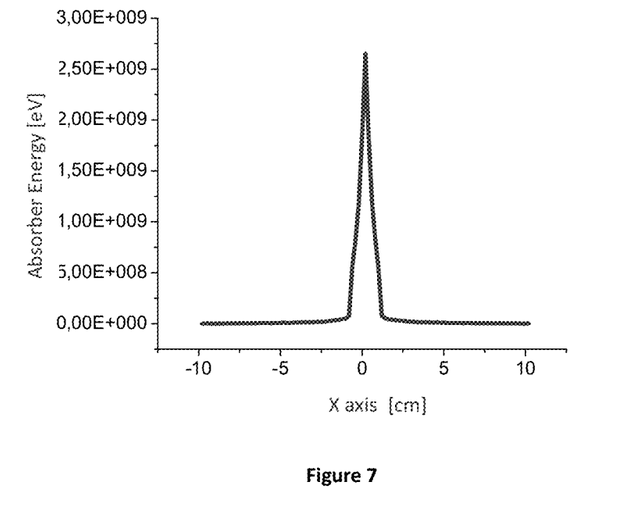
FIG. 7 shows a profile of the energy deposited at low energy (per voxel unit) (Z=0, Y=0) with angular collimator acceptance: polar: 2 degrees and azimuthal: 2 degrees. E=4 MeV.
Figure 8:
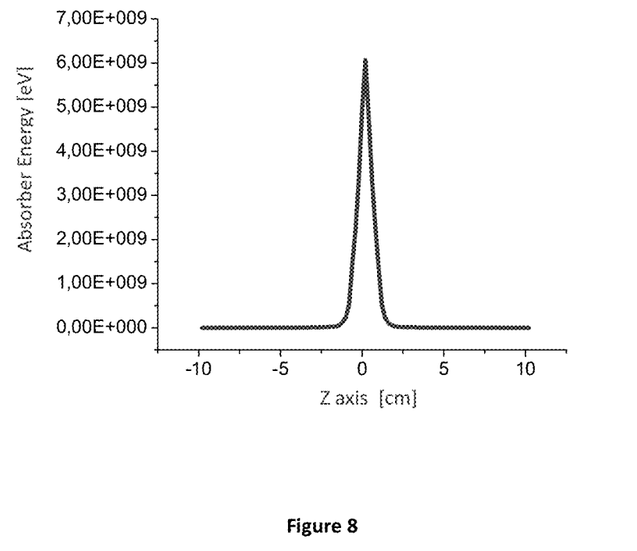
FIG. 8 shows a profile of the energy deposited at high energy (per voxel unit) (Z=0, Y=0) with angular collimator acceptance: polar: 2 degrees and azimuthal: 2 degrees. E=4 MeV.

When this beam is pointed virtually towards a water phantom or water equivalent, a depth dose profile can be obtained like the one shown in FIG. 4 for two different energies. These profiles were achieved using a MCS code. Other results attained by MCS are shown from FIGS. 5 to 8. All the MCS that were carried out show that the convergent radiotherapy technique, as proposed with this invention, is noticeably better than the conventional techniques used to date.

A very brief description of the positioning system for the various cases is given in this presentation of the invention. Directional arrows are also shown without providing further details, as that would not be part of the essence of this invention. Also, positioning systems are already available on the market. However, the various ways in which the invention must be adapted in each case shall be presented.

BRIEF DESCRIPTION OF THE DRAWINGS

Additionally, a sensor system (37), with position sensors can be located on the patient's skin aimed to provide spatial positioning information; automatic systems based on the spatial position dedicated to control electro-mechanic devices.

DETAILED DESCRIPTION OF THE INVENTION

The invention presented here consists of a device that generates a convergent electron and X-ray beam. First, an electron beam from electron cannon is needed. The electrons are accelerated in radiotherapy LINAC (or simply LINAC) by a series of stages until a flow of electrons with energy between 6 and 18 MeV is achieved. It can also be used for intermediate or low energy ranges generated solely by means of the electron cannon.

Figure 12:
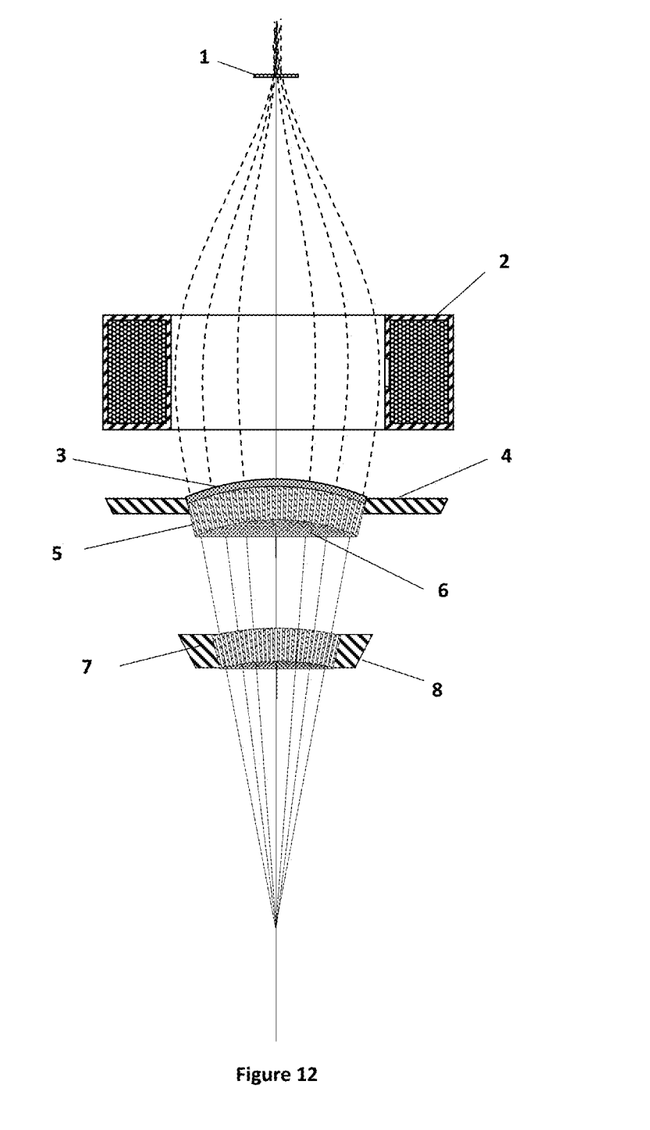
FIG. 12 shows a sketch of the present invention's essential functional parts: electron disperser (1), set of magnet or electrostatic lens (2), anode cap (3), shielding ring support (4), poli-collimator (5), holes (6), optional second poli-collimator (7) and conical ring for penumbra (8).

As seen in FIG. 12, the relatively collimated electron beam coming from the electron linear accelerator is first expanded by an electron disperser (1). The electrons are then focalized by the action of an appropriate set electro magnet or electrostatic lens controlled by electric current and/or voltage respectively (2). The electrons that emerge from the lens intercept the surface of an anode shaped as a curved (spherical, aspheric or parabolic) cap, which shall be referred to as an "anode cap" (3) and attached to shielding ring support (4). The anode cap's curvature radius defines the focal distance of the convergent system.

Figure 9:
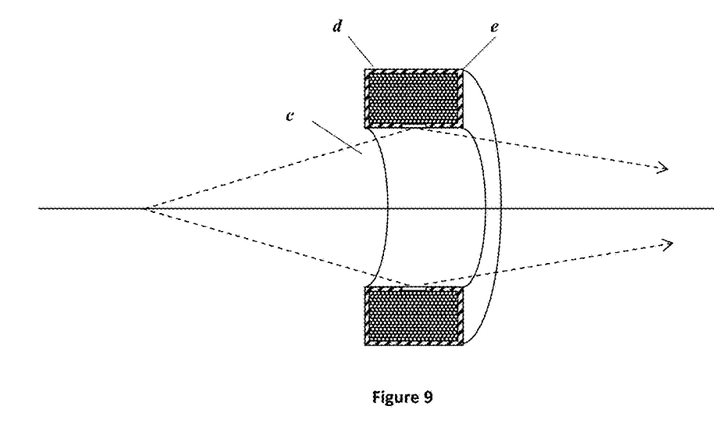
FIG. 9 shows a sketch of the convergent electron beam generator element, which can be made up of more than one magnetic lens.

As shown in FIG. 9, the magnetic lens has an entrance lens body (c), a field concentrator housing (d) and electric conductors with a solenoid winding (e).

Figure 10:
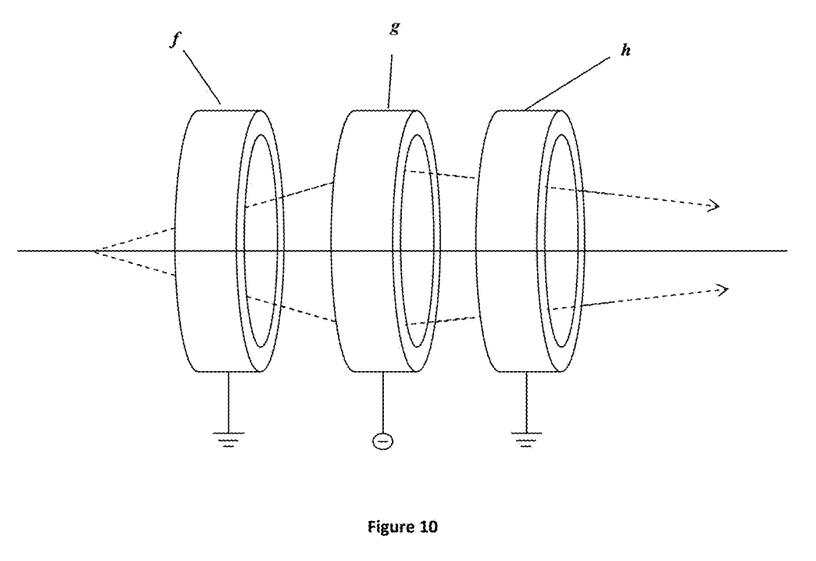
FIG. 10 shows a sketch of an alternate configuration of the convergent electron beam generator element, which can be made up of an electrostatic element similar to cylinder lenses.

The convergent electron beam generator element, in an alternative configuration of the invention, can also be made up of an electrostatic element that is similar to cylinder lenses. The first is grounded (f), the second cylinder is negatively polarized (g), and the third is also grounded (h) (FIG. 10).

Figure 11:
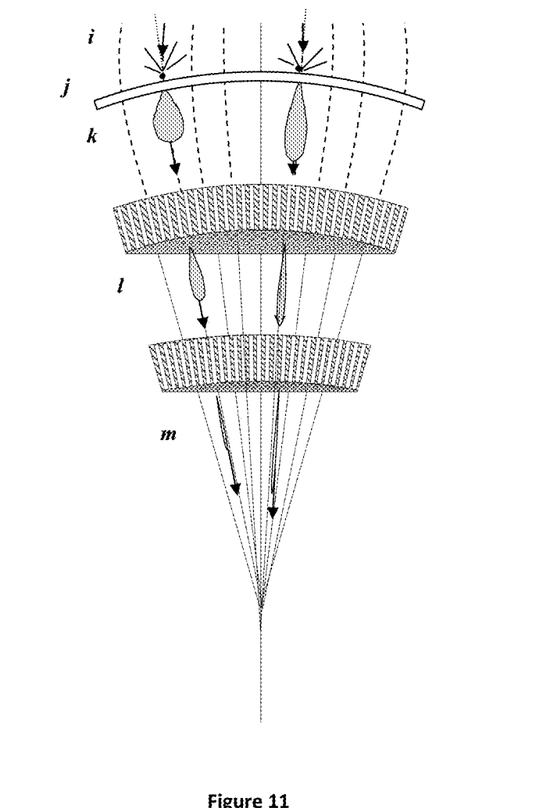
FIG. 11 shows a sketch describing how the convergent photon beam is generated by the invention proposed here.

The electronic lenses must be adjusted so that the electron beam impacts perpendicularly on the entire surface of the anode cap. As a result of the interaction of the electrons with the atoms that make up the anode's material, breaking radiation (known as bremsstrahlung), or X-rays in the material, is generated. As the incidence of the electrons occurs on the entire surface of the anode cap (i) (see FIG. 11), the bremsstrahlung X-ray emission phenomenon will occur isotropically on the entire anode cap. Bremsstrahlung is generated at each point on the cap. According to FIG. 11, the X-rays that exit the anode cap have an angular non-isotropic distribution, with a greater intensity in the electrons' incidence direction and an angular divergence inversely proportional to the incident electron's energy (k). The X-rays are then collimated by a spherical poli-collimator (5) (similar to the anode cap) with tens, or hundreds of small holes (6) having millimetric or submillimetric dimensions according to the requirements. These holes point in the direction of the focal point, which represents the geometrical convergence focus of the anode cap, i.e. "anode cap focal point" (n). The X-rays that are able to pass through these holes will exit with a much lower angular dispersion than they had at the anode cap (3) exit. The rest are absorbed into the material, thus generating a convergent photon beam, with its greatest intensity concentrated at the focal point. The definition of the focal point of this convergent photon beam may be improved by inserting an optional second poli-collimator (7). This effect globally generates a radiation volume that mainly points towards the system's focal point with a significantly greater intensity of X-rays at the focal point (peak-focus), the magnitude of which will depend upon the energy of the electrons, the curvature radius of the anode cap (3), the anode cap's surface and the opening of the set of superimposed diaphragms that will be shown further on.

The invention's essential parts are shown in FIG. 12. Electrons coming from an electron source are dispersed by a small sheet (scattering foil) (1) in order to generate a flow of divergent electrons. The electrons are deflected according to the axis by a magnetic (or electrostatic) lens (2), thus generating a flow of convergent electrons (i) that is perpendicularly intercepted (j) by the anode cap (3), and a shielding ring support (4). The X-rays that are able to exit the thickness of the anode cap (k) are collimated by a poli-collimator (5) having small holes perforated, tens or hundreds, on its entire surface (6) that point in the direction of the focal point. The convergent X-ray beam (l) can be collimated once again (m) by an optional second poli-collimator (7). This collimator is surrounded by a concentric conical ring for penumbra (8). The poli-collimator can be either adhered to or separate from the anode cap. The material from which the polli-colimator is made is of a certain composition and thickness, such that the collimator is able to completely attenuate the X-rays that impact outside the collimator's holes and the holes can be either cylindrical or conical.

Figure 13:
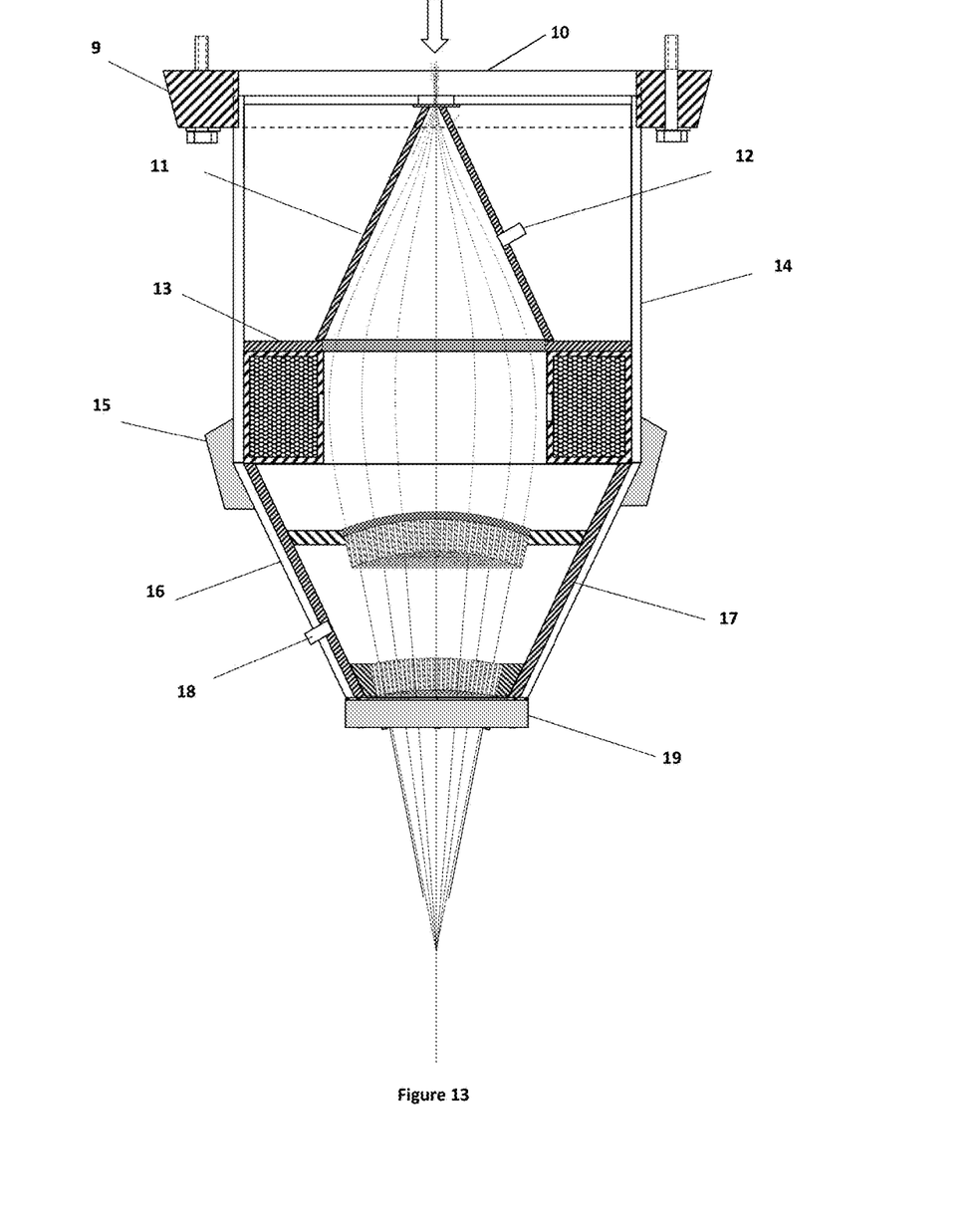
FIG. 13 shows a detailed description of some specific parts of the invention, including each of its parts: electron source coupler (9), electron entering window (10), cone-shaped shielding (11), vacuum connection I (12), ring-shaped support (13), cylindrical external housing (14), phase coupler (15), truncated cone (16), internal shielding (17), vacuum connection II (18) and front-end unit (19).

FIG. 13 shows the invention as an apparatus in more detail. It has an electron source coupler (9), which allows the device to be attached to a specific LINAC (high energy) or any kind of electron cannon (low energy) by means of screws for example, as shown. Whichever the case, it is a piece that must adapt to the different devices available on the market. When considering LINAC as electron source, there is the electron entering window (10). Contrary, when using electron cannon as electron source it is not required the insertion of electron disperser (1) that acts as scattering foil. The electron beam enters a vacuum space contained by a cone-shaped shielding (11), with a vacuum connection I (12) and at the base of the cone there is a ring-shaped support (13) that attaches to the cylindrical external housing (14). Further down is a phase coupler (15) that separates the regions where electron and photon beams are transported. The photon region is made up of an external housing shaped like a truncated cone (16) that has internal shielding (17) with shielding ring support (4) and conical ring for penumbra (8) as well as a vacuum connection II (18) if required. Finally, there is a front-end unit (19) at the inferior end of the truncated cone (16). The details of front-end unit (19) are described below.

Figure 14:
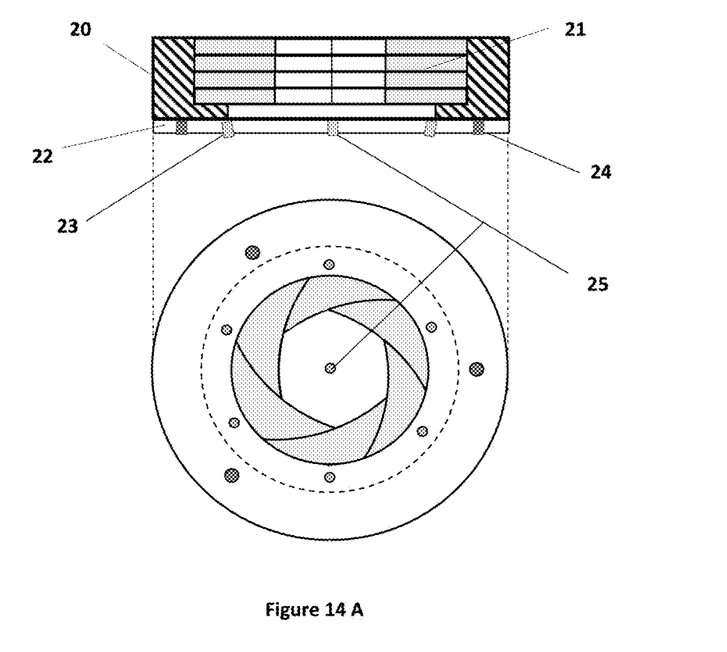
FIGS. 14a and 14b show a sectional view and front view, respectively, of the front-end unit, comprising: an exit collimator with collimator support (20) and set superimposed diaphragms (21), light supporting plate (22), with positioning laser guide (23), position control sensors (24), and, and central laser (25).

FIGS. 14a and 14b show two views of the front-end unit (19), which is made up of: an exit collimator comprising by a collimator support (20) and a set of superimposed diaphragms (21). The collimator regulates field size at the incident surface trough the set of superimposed diaphragms placing one on top of the other, as sketched in Figure. In order to mark the entry field on the surface of the patient, there is a light supporting plate (22) made out of a low Z (atomic number) material, such as acrylic, with holes where positioning laser guide (23), are placed that point in the focal point's direction. These are located along a circumference on the border of the field diaphragm, enabling visibility of the entry field upon the patient's skin undergoing irradiation. Also position control sensors (24) are located in the light supporting plate. Finally, in order to locate central axis, the front-end unit has the small removable central laser (24).

Figure 15:
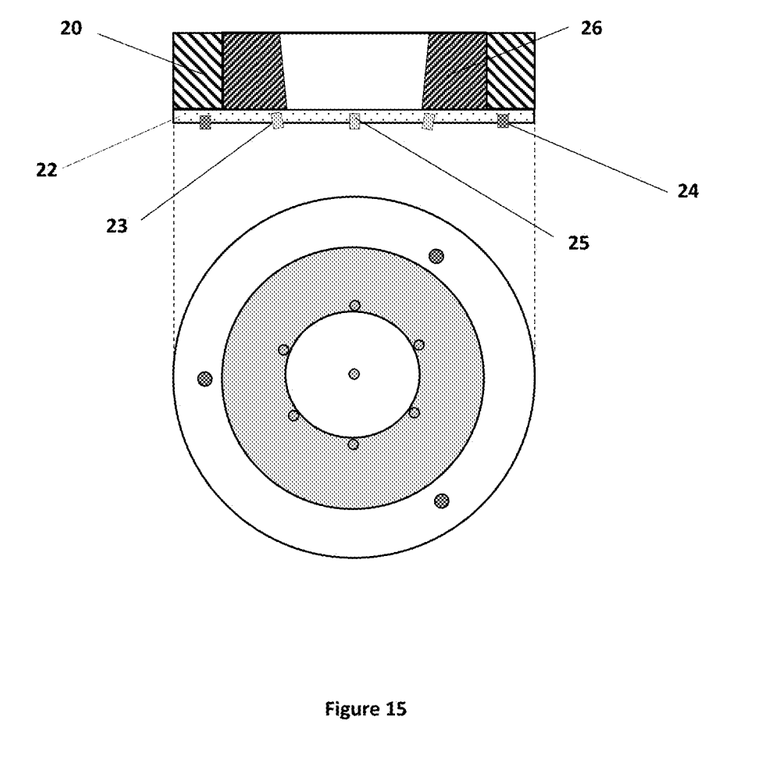
FIG. 15 shows a sectional view of an alternative configuration of the front-end unit, with interchangeable conical ring collimator (26).

FIG. 15 shows a view of an alternate of the front-end unit in which diaphragms are replaced by a solid interchangeable conical ring collimator (26) that has a predefined field size. The surrounding positioning lasers (23), central laser (25) and position control sensors (24) can be incorporated to the light supporting plate.

Figure 16:
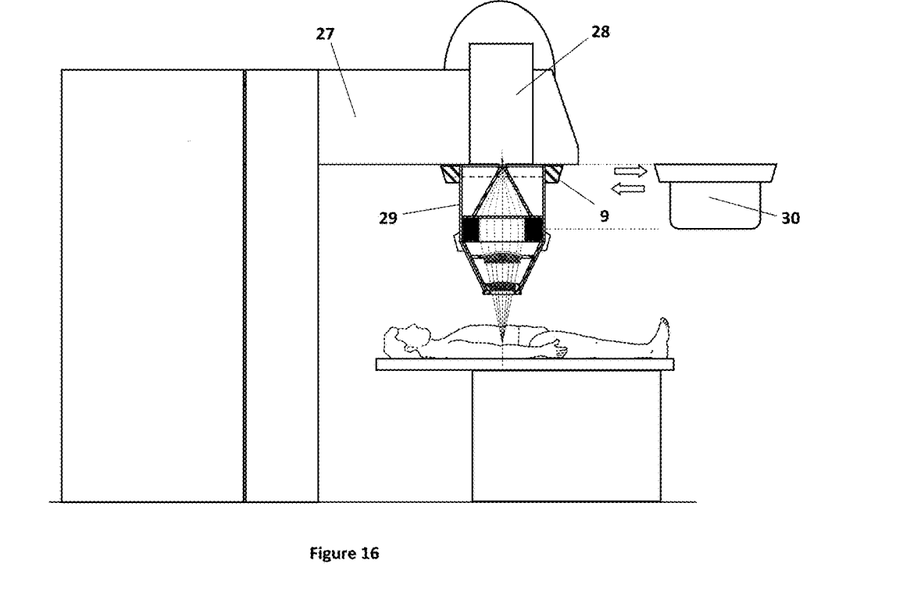
FIG. 16 shows a configuration of the present invention adapted to a typical LINAC, with: gantry (27), electron linear accelerator (28), convergent device (29), which constitutes the invention proposed here, and conventional head (30).
Figure 17:
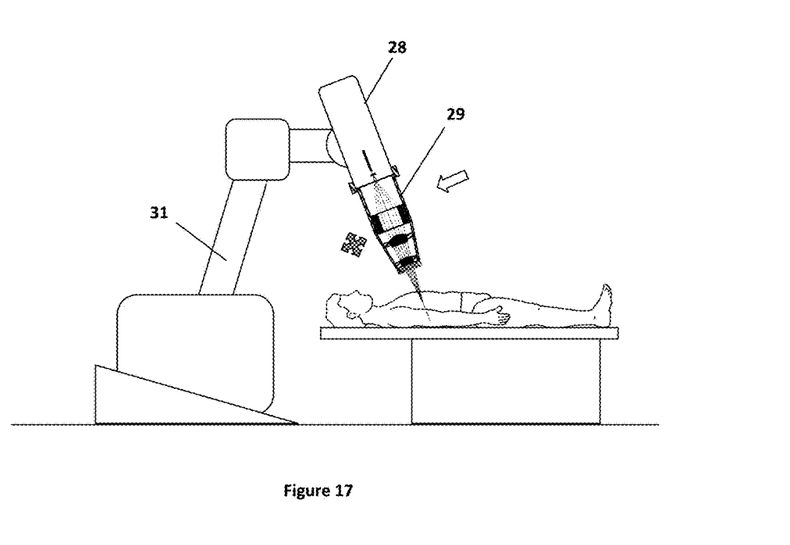
FIG. 17 shows a configuration of the convergent device (29) adapted to a Cyberknife robotic system (31) and electron linear accelerator (28).
Figure 18:
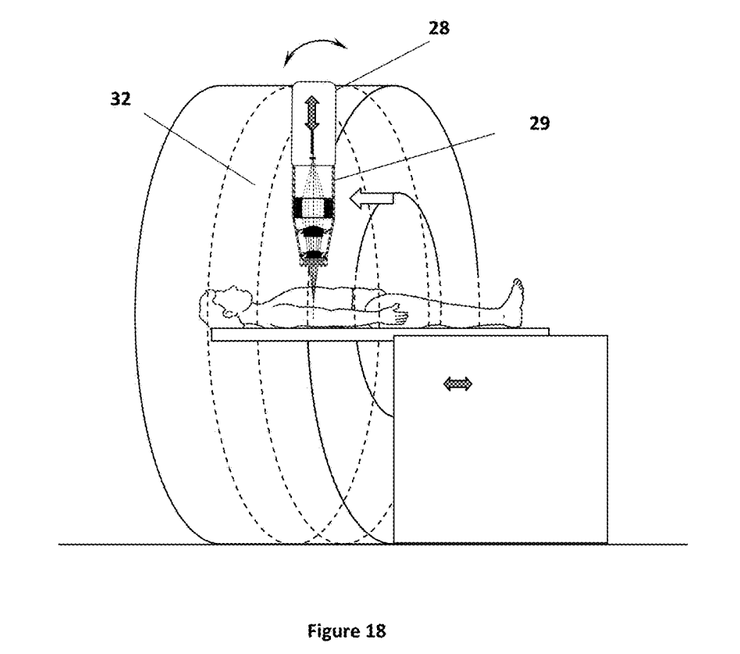
FIG. 18 shows a configuration of the convergent device (29) adapted to a Tomotherapy system that comprises a rotation system (32) and electron linear accelerator (28).

FIGS. 16, 17 and 18 illustrate how this invention could be adapted to apparatuses currently in use for external photon radiotherapy. FIG. 16 exhibits the invention adapted to a conventional LINAC, showing a gantry (27) and the electron linear accelerator (28). Figure includes also a sketch of the convergent device (29) proposed here that is joint firmly through electron source coupler (9), in the same location where the conventional head (30) is attached, as shown in FIG. 16. The figure also sketches how the conventional head (30) and the convergent device can be exchanged.

FIG. 17 shows a configuration of the convergent device (29) adapted to a Cyberknife: robotic system (31) that includes a, linear accelerator (28) and the convergent device.

FIG. 18 displays a configuration of the convergent device (29) adapted to a Tomotherapy device that comprises a rotation system (32) an electron linear accelerator (28) and the convergent device (29).

The above means that the convergent device (29) can be built a certain size so that it is adjustable to the dimensions of the currently commercially available technologies.

Figure 19:
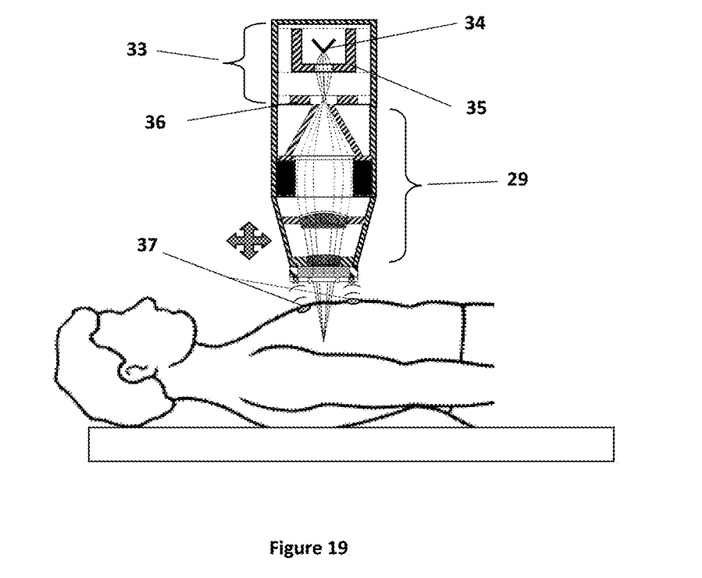
FIG. 19 shows an alternate configuration of the convergent device (29) being used for low energy application that is made up of electron cannon (33) comprised of: filament (34), concentrator cathode (35), and disperser anode (36).

FIG. 19 shows a prototype for electron sources with low energies (<1 MeV). This prototype is made up of the electron cannon (33) and the convergent device (29) being proposed. Typical electron cannons are comprised of a filament (34), a concentrator cathode (35) and disperser anode (36). The prototype is also equipped with sensor systems (37) for feedback positioning using the devices described above as well as sensors adhered to the patient's skin (similar to a bandage). Additional advantages that a unit such as this one has to offer are its noteworthy low cost, small size and fewer shield requirements, thus making external photon radiotherapy an effective, low-cost technique available to a greater number of people. Likewise the entire system, electron cannon and convergent device, constitutes an ensemble that becomes a stand-alone convergent beam device.

Figure 20:
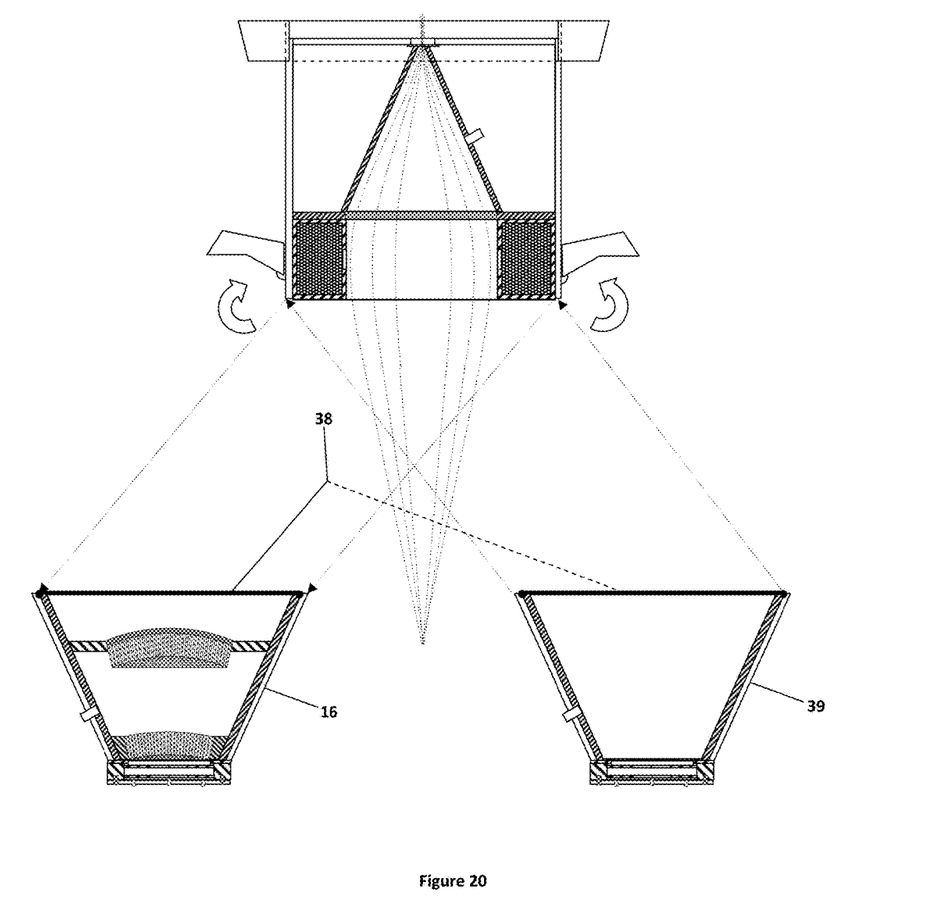
FIG. 20 sketches how photon/electron convergent exit beams are exchangeable by means of different cones: convergent device (29), phase coupler (15), vacuum ring seal (38), truncated cone (16) and empty truncated cone (39).

Lastly, the description in FIG. 20 explains how the radiation modality of the proposed convergent device (29) can be simply converted to a convergent electron beam by exchanging through the phase coupler (15) the truncated cone (16) by empty truncate cone (39) that consists of a similar piece as 16 without anode and collimators, as shown.

The invention claimed is:

1. A convergent X-ray beam-generating device, comprising:
    an electron disperser element for dispersing an electron beam from an electron source,
    one or more magnetic and/or electric lenses for expanding and redirecting the electron beam,
    an anode cap made of a material and thickness, and having a cone shape and a focal point such that an X-ray radiation is generated on the entire surface of said anode cap, wherein the X-ray radiation is emitted forward, focusing mainly at the focal point of the anode cap, and
    a coaxial poli-collimator having the same shape as that of the anode cap, with multiple holes for collimating and focusing the X-ray radiation at the focal point of the anode cap.

2. A device according to claim 1, comprising an electron lens system comprising:
    an electromagnet lens controlled by electric current; and/or
    an electrostatic and/or electric condenser controlled by voltage.

3. A device according to claim 1, wherein the anode cap can be spherical, aspherical, parabolic or another shape with a geometry that has a focal point.

4. A device according to claim 1 wherein the poli-collimator has tens or hundreds of holes aiming in the direction of the focal point.

5. A device according to claim 1 wherein the poli-collimator can be either adhered to or separate from the anode cap.

6. A device according to claim 1 wherein the material from which the collimator is made is of a certain composition and thickness, such that the collimator is able to completely attenuate the X-rays that impact outside the collimator's holes and the holes can be either cylindrical or conical.

* * * * *